United States Patent [19]
Wallach et al.

[11] Patent Number: 6,090,923
[45] Date of Patent: Jul. 18, 2000

[54] MURINE MONOCLONAL ANTIBODY BINDING TNFα

[75] Inventors: David Wallach; Talia Hahn; Zelig Eshhar, all of Rehovot, Israel

[73] Assignee: Yeda Research And Development Co. Ltd., Rehovot, Israel

[21] Appl. No.: 07/794,365

[22] Filed: Nov. 13, 1991

Related U.S. Application Data

[63] Continuation of application No. 07/351,290, May 8, 1989, abandoned, which is a continuation of application No. 06/808,262, Dec. 12, 1985, abandoned.

[30] Foreign Application Priority Data

Dec. 20, 1984 [IL] Israel .......................................... 73883

[51] Int. Cl.$^7$ ............................ C07K 16/18; C07K 16/24
[52] U.S. Cl. ................................. 530/388.23; 530/387.1; 530/388.2; 530/388.24; 530/388.85; 435/70.21
[58] Field of Search ............................... 435/70.21, 70.2, 435/172.3, 240.26, 240.27; 530/387, 837, 838; 935/95, 103, 104

[56] References Cited

U.S. PATENT DOCUMENTS

| | | |
|---|---|---|
| 4,684,623 | 8/1987 | Larrick et al. ............................ 514/14 |
| 4,879,226 | 11/1989 | Wallace . |
| 4,880,915 | 11/1989 | Kajihara et al. . |
| 5,654,407 | 8/1997 | Boyle et al. . |
| 5,672,347 | 9/1997 | Aggarwal et al. ................... 424/139.1 |
| 5,698,419 | 12/1997 | Wolpe et al. . |
| 5,795,967 | 8/1998 | Aggarwal et al. . |

FOREIGN PATENT DOCUMENTS

| | | |
|---|---|---|
| 117705 | of 0000 | European Pat. Off. ..... A61K 39/395 |
| 168214 | of 0000 | European Pat. Off. .......... C07K 3/18 |
| 59-246184 | 11/1984 | Japan . |

OTHER PUBLICATIONS

Adevka et al Antiviral Res. 5/Suppl 1:141–48, 1985.
Matthews et al Immunol. 48:321–27, 1983.
De St Goth et al J. Immunol. Meth. 35:1–21, 1980.
De St Groth, J. of Imm. Metho 35:1–21 (1980) "Production of Monoclonal Antibodies".
Wallach et al, "Regulatory Determinants in the Function and Formation of Human Lymphotoxins Applied For Developing Monoclonal Antibodies Against These Proteins." 4$^{th}$ International Lymphokine Workshop on Molecular and Cellular Biology of Lymphokines, Oct. 17–24, 1984. Lymphokine Res. 3(4) 1984.
Hahn et al, Use of monoclonal antibodies to a human cytotoxin for its isolation and for examining the self–induction of resistance to this protein PNAS, V. 82 pp. 3814–3818, Jun. 1985.
Matthews, Effect on human monocyte killing of tumour cells of antibody raised against an extracellular monocyte cytotoxin, Immunology v. 48, pp. 321–327, 1983.
Kohler and Milstein, Continuous cultures of fused cells secreting antibody of predefined specificity, Nature V.256, 1975.
Bringman et al, "Antigenic Distinction between Human Lymphotoxin and Tumor Necrosis Factor Defined with Monoclonal Antibodies," Hybridoma, V4, 85, 1985.
Hass et al, "Characterization of Specific High Affinity Receptors for Human Tumor Necrosis Factor on Mouse Fibroblasts," J.Biol.Chem., V. 260, 12214–18, 1985.
Aderka, et al.; Tumor Necrosis Factor Induction By Sendai Virus; J. Immunol.; 136(8):2938–42 (1986).
Pennica, et al.; Human Tumor Necrosis Factor:Precursor Structure, Expression. and Homology to Lymphotoxin; Nature; 312:724–8 (1984).
Aggarwalt, et al.; Human Tumor Necrosis Factor; J. Biol. Chem.; 260:2345–54 (1985).
Old, L.J.; Tumor Necrosis Factor (TNF); Science; 230:630–32 (1985).

*Primary Examiner*—Nancy A. Johnson
*Attorney, Agent, or Firm*—Browdy and Neimark

[57] ABSTRACT

A cytotoxic protein expressed by human peripheral blood mononuclear cells is isolated in essentially homogenous form. This protein may be used to elicit production of polyclonal or monoclonal anti-cytotoxin antibodies.

Hybridomas secreting anti-cytotoxin antibodies are identified by a solid phase bioassay. The antibodies are useful in the immunopurification of cytotoxins. The purified cytotoxic proteins are useful for the treatment of virus-infected or tumor target cells, either alone or in combination with interferon or a metabolic blocker.

12 Claims, 6 Drawing Sheets

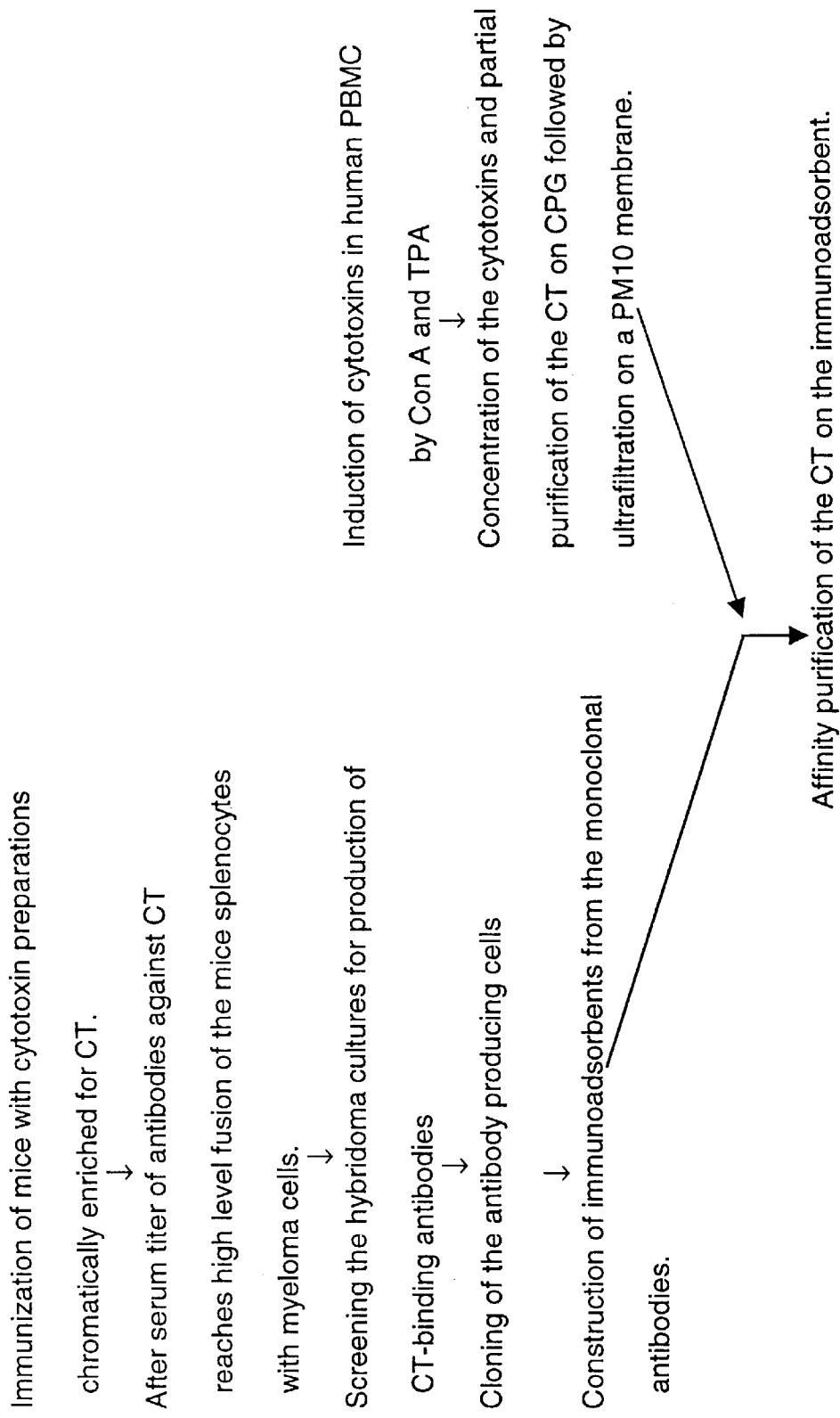

FIG. 2A

Neutralization assay: Incubation of CT preparation with antiserum. → Determination of CT activity (in the presence of antiserum)

FIG. 2B

Binding assay: Incubation of CT preparation with antiserum → Precipitation of serum immunoglobulin+bound CT with goat antiserum against mouse immuno-globulins → Washing of immuno precipitate followed by its solubilization at 0.075M ammonia → Determination of T activity in solubilized immunoprecipitate

FIG. 3

Adsorbtion of hybridoma produced immunoglobulin to PVC microwells which had been precoated with affinity purified antibodies against mouse immunoglobulins. → Incubation of CT preparations in microwells. → Rinsing of microwells followed by dissociation of bound antigens at 0.075M ammonia → Determination of CT activity in the proteins eluted form microwells

MURINE MONOCLONAL ANTIBODY BINDING TNFα

This application is a continuation of application Ser. No. 07/351,290, filed May 8, 1989, now abandoned, which is a continuation of Ser. No. 06/808,262, filed Dec. 12, 1985 now abandoned.

FIELD OF THE INVENTION

There is provided in purified form a cytotoxic protein, CT, originating in human mononuclear cells. There is also provided a process for preparing such purified CT in essentially homogenous form. There is also provided an immunoassay for the screening of hybridoma cultures in order to locate cultures producing antibodies capable of binding CT. Further, according to the invention there is provided a monoclonal antibody CT-1 specific for the CT. There is also provided a pharmaceutical composition useful for selectively treating virus infected and tumor target cells in humans which comprises CT or a salt or derivative thereof and a pharmaceutically acceptable carrier.

BACKGROUND OF THE INVENTION

Proteins which exert a toxic effect on cells were found to be secreted, in response to stimulation, by mononuclear cells of various kinds. T-cells, or probably both the helper and the suppressor subsets can respond to antigens recognized by them, as well as to mitogenic lectins, by secreting such cytotoxic proteins (Granger, G. A. and Kolb, W. P., J. Imminol. 101, 111–120 (1968); Ruddle, N. H. and Waksman, B. H. J. Exp. Med. 128, 1267–1275 (1968); Eardley, D. D., Shen, F. W., Gershon, R. K. and Ruddle, N. H., J. Immunol. 124, 1199–1202 (1980)).

Monocytes and macrophages produce cytotoxic proteins in response to certain bacterial toxins (reviewed by Ruff, M. R. and G. E. Gifford in Lymphotoxins, E. Pick and M. Landy editors, Academic Press, Inc. New York, 235–272, (1981)). Natural killer cells secret cytotoxic proteins upon incubation with appropriate target cells (Wright, S. C. and Bonavia, B., J. Immunol. 129, 433–439, (1982)) while cells of certain continuous B lymphocyte lines were found to produce spontaneously cytotoxic proteins (Rosenau, W., Stites, D. and Jemtrud S., Cell. Immunol. 43, 235–244, (1979)). Proteins produced in lymphocyte cultures are usually referred to as "lymphotoxins", while the term "tumor necrosis factor" is often used for cytotoxic proteins produced in cultures of monocytes or of macrophages. Evidence has been presented that such cytotoxic proteins can selectively destroy tumor cells (Rundel, J. O. and Evans, C. H., Immunophormacol, 3, 9–18, (1981). So far, only a single protein of this type, produced spontaneously by cells of a B lymphocyte line has been characterized in some detail. It was purified to homogeneity and its molecular weight was estimated to be about 20,000 daltons (Aggarwal, B. B., Moffat, B. and Harkins, R. N., J. Biol. Chem. 259, 686–691 (1984)).

SUMMARY OF THE INVENTION

There is provided a purified cytotoxic protein referred to as cytotoxin (CT) and a procedure for effectively inducing this protein in monocytes or in cells derived from monocytes by virus such as Sendai virus. There is further provided a process for preparing such purified, essentially homogeneous CT, naturally produced by peripheral mononuclear blood cells. The purified CT has a M. W. of about 17,000 daltons. CT can be isolated by the use of monoclonal antibodies against such CT which can be obtained form mice injected with partially purified or crude preparations of CT. There is provided a technique for establishing lines of lymphocytes producing such anti-CT antibodies. Such lines are advantageously established by screening a plurality of hybridomas derived from splenocytes of such immunized mice. There is also provided a monoclonal antibody specific for CT. Such monoclonal antibody is produced by such hybridoma cell lines and is used for isolating CT in substantially homogeneous purified form.

The thus obtained purified cytotoxin, CT, is recognized by a specific anti-CT antibody. It has a M. W. of about 17,000±500 daltons, as determined by analytical polyacrylamide SDS gel electrophoresis. There are also provided pharmaceutical compositions useful for selectively treating virus infected cells and tumor target cells in humans which comprises CT or a salt or derivative thereof, and a pharmaceutically acceptable carrier.

The term "salt" refers to salts of either or both the carboxyl and the amino groups of CT, and the term "derivatives"—to covalent modifications of the polypeptide side chains of the CT. The nature of the carrier for the CT, salt or derivative depends on the way it is applied for therapeutic purposes—be it in the form of a cream or lotion—for topical application or in the form of liquid, in which the CT, salt of derivative will be stabilized by adding components such as human serum albumin, for injection or for oral application. The purified CT is effectively cytotoxic to tumor and to virus infected cells at concentrations as low as 10 picograms/ml. The amounts of CT applied for therapy will be adjusted to reach such range of concentrations, or higher ones, in the target tissues.

The said CT is effectively cytotoxic to cells in the presence of metabolic blockers such as cycloheximide (CHI), Actinomycin D or Mitomycin C but in the absence of these agents cells of many kinds exhibit resistance to its cytotoxic effect. Infection by viruses can also render cells vulnerable to killing by the said CT. It effectively enhances, for example, the killing of VSV infected SV-80 cells while having no cytotoxic effect on uninfected SV-80 cells. Killing of virus infected cells by the said CT is potentiated by IFNs, primarily by IFN-γ, when those are applied at substantial concentrations. Thus, in applying the said CT for therapy, pharmaceutical compositions containing also a suitable IFN are of advantage, and so are also pharmaceutical compositions containing metabolic blockers such as CHI, Actinomycin D or Mitomycin C.

Hybridoma cells producing the antibodies against CT were deposited with the International Culture Collection of Institute Pasteur, Paris, France, under Deposition No. I-472, deposited on Jul. 16, 1985, designated by us as Cell Line CT-1.

BRIEF DESCRIPTION OF THE DRAWINGS

The invention is illustrated in the following by way of example.

FIG. 1 is a scheme illustrating the technique of isolation of CT. As shown the process steps involve immunizing a suitable laboratory animal (mice, etc.) with preparations enriched with CT by chromatographic procedures, followed by monitoring serum titers of CT-neutralizing and CT-binding antibodies by the techniques set out in FIGS. 2a and 2b. Hybridomas derived from spenocytes of the immunized mice were screened for the production of CT-binding antibodies by the procedures set out in FIG. 3. Hybridomas found to produce such antibodies were cloned and the monoclonal antibodies produced were applied to immunoadsorbent columns on which CT was affinity-purified from preparations of lymphokines which had been induced in PBMC by concanavalin A (Con A) and phorbol-12-O-myristate 13 acetate (TPA) and then partially purified by chromatography on controlled-pore glass. The critical step was the screening of a large number of hybridoma cultures for detecting a few producing antibodies against CT. The technique developed for that purpose (set out in FIG. 3) involves a solid phase CT-binding assay, which allows a rapid screening of hybridoma cultures for the presence of such antibodies, followed by a bioassay by which CTs bound to the solid phase can be sensitively detected, using cells sensitized to the cytotoxic effect of CT by cycloheximide.

DESCRIPTION OF THE PREFERRED EMBODIMENT

Figure 4A:
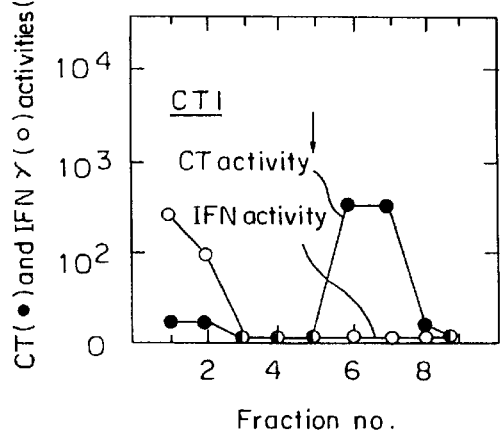
FIG. 4. demonstrates the selectivity in the binding activity of a monoclonal antibody thus isolated, comparing CT-binding to a binding of interferon-γ by immunoadsorbents contructed form this antibody (A), as well as from two other unrelated monoclonal antibodies (B, C). It shows that of these three antibodies only one binds CT, namely, that which is directed against CT (CT-1 in FIG. 4A). It also shows that this binding of CT occurs without binding any detectable amounts of another protein in the cytotoxin preparation-IFN-γ. Under the same conditions of experiment a monclonal antibody against the latter, shown in B, does bind effectively IFN-γ without binding CT at all.
Figure 4B:
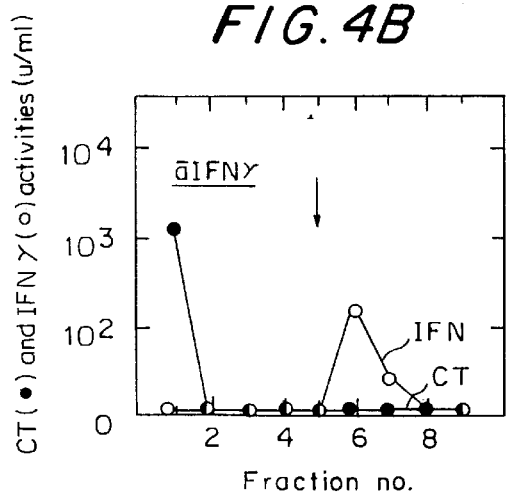
Figure 4C:
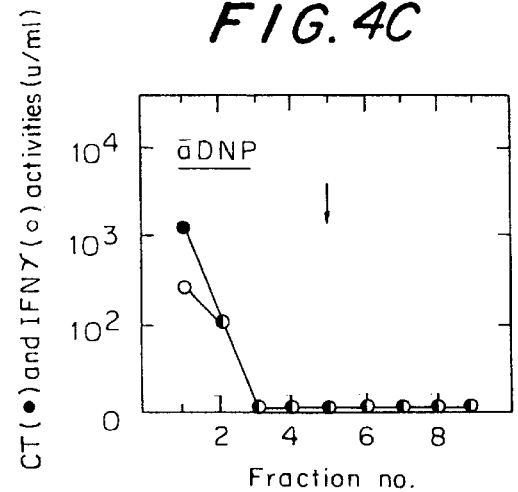

The following example is given for illustration only.

1. Induction of CT: Human peripheral blood mononuclear cells (PBMC) are isolated on "Ficoll-Hypaque" (Pharmacia, Upsala, Sweden) from the "buffy-coats" of freshly donated blood and depleted of platelets by differential centrifugation. The cells are suspended at a concentration of $10^7$ cells/ml and incubated at 37° C. in MEM alpha medium (Gibco, Grand Island, N.Y.). CT is induced in these cells by one of the following techniques:

A. Preparations used for the immunization of mice are induced by stimulating PBMC with phytohemagglutinin-P (PHA). Prior to that stimulation the cells are first incubated for 12 h in the presence of a crude preparation of lymphokines (0.2 μg/ml). This treatment, does not result in the production of CT but greatly increases the responsiveness of the cells to subsequent stimulation. PHA (5 μg/ml) (Difco, Detroit) is then added and the PBMC are further incubated for 24 h. The medium is then collected, centrifuged at 2500 rpm for 15 min to remove cell debris, and processed for concentrating and enriching the CT as described below.

B. Preparations of lymphokines used for purifying CT on immunoadsorbents are advantageously induced with Con-A as it was found difficult to fully eliminate traces of PHA in the purification procedure. The cells are first treated for 12 h with 0.25 μg/ml Con-A. At this concentration Con-A does not induce significant secretion of CT but it increases the responsiveness of the cells to subsequent stimulation by a higher concentration of Con-A. Phorbol-12-0-myristate 13 acetate (TPA) is then added to a concentration of 5 ng/ml. and 3 h later Con-A us added to concentration of 10 μg/ml. The cells are incubated for 24 h and then, following replacement with fresh media containing 5 μg/ml Con-A for a further period of 24 h. The media are combined and centrifuged, methyl α-D Mannoside (Sigma, St. Louis, Mo.) is added to a concentration of 50 mM and the media are then further processed for purification on the immunoadsorbent as described below.

C. Alternatively the CT can effectively be induced in human peripheral-blood mononuclear cells, in monocytes isolated from the mononuclear cell population or in cultured cells such as Ug37 whose properties resemble those of monocytes by applying to these cells Sendai virus (200 HAU/ml) and incubating the cells for a period of about 12 hours to allow the production of CT. The cell media are then centrifuged and processed for purification of the CT as described below.

2). Quantitation of CT: CT is quantitated by determining its cytotoxic effect by a bioassay (Wallach, D., J. Immunol. 132, 2464–2469 (1984)). Samples to be tested are applied in several serial dilutions simultaneously with the application of cycloheximide (CHI 50 μg/ml) into micro-wells containing confluent cultures of the SV-80 cells. The extent of cell killing, determined by measuring the uptake of neutral-red by the cells, is quantitated 20 hours later, by using a MicroELISA Autoreader (Dynatech, Alexandria, Va.).

3. Chromatographic Enrichment of CT: Crude preparations of CT are first concentrated by adsorption to controlled pore glass (CPG) (PG-350-200 Sigma St. Louis, Mo.) followed by desorption in 0.5 M tetramethyl ammonium chloride (TMAC) and then further concentrated by ultrafiltration with an Amicon PM-10 membrane (Amicon, Denvers, Mass.). CT preparations applied for immunization of mice are then further purified by one of the two following procedures:

(A) CPG-concentrated CT preparations are fractionated by electrophoresis on 7.5% acrylamide gels, under non-denaturating conditions (Walker, S. M. and Lucas, Z. J., J. Immunol. 113, 813–823, (1974), Lewis, J. E., Carmack, C. E., Yamamoto, R. and Granger, G. A., J. Immunol. Meth. 14, 163–176 (1977)). Fractions eluted from slices of the gels, which exhibit cytotoxic activity are pooled, concentrated by ultrafiltration on a PM-10 membrane and injected into mice.

(B) CPG-concentrated CT preparations are equilibrated with 1 M NaCl, 30% ethylene glycol, 10 mM sodium phosphate and 0.1 mM EDTA and subjected twice, sequentially, to fractionation on Ultrogel AcA44. Following each fractionation, fractions exhibiting cytotoxic activity are pooled and concentrated on a PM-10 membrane. The cytotoxic proteins recovered from the second run on the Ultrogel column are applied to further purification by preparative isoelectrofocusing on a 1% ampholine gradient (pH 3.5–10) constructed in sucrose solution using an LKB 8100-1 column. Fractions exhibiting maximal cytotoxic activity, peaking at about pH 6.4 are pooled, concentrated, equilibrated with PBS and then injected into mice.

Immunization with CT and Cell Fusion

Four month old female CB6 mice are injected with samples of 10 μg of CT preparations—five injections with CT enriched by procedure A, as described above, and another two injections with CT enriched by procedure B. In the first immunization, the proteins are emulsified in complete Freund's adjuvant and injected into the foot pads of the mice (0.5 ml/mouse). The second injection, is given 3 weeks later, and the rest of the injections which are given at 1 to 2 week intervals, are all given subcutaneously using alumina gel as adjuvant (0.3 μg/0.25 ml/mouse). Immunization is then discontinued for a month and the mouse showing the highest titer of serum antibodies against CT is injected twice, intraperitoneally, at a 1 day interval, with 10 μg of a CT preparation enriched by procedure B. A day after the second immunization, the mouse is sacrificed and its splenocytes are fused with myeloma cells. The fused cells are distributed into multiple wells of microtiter plates and hybridomas are selected for in HAT-containing tissue culture medium. Hybridomas found to produce antibodies against CT are cloned in soft agar. For growing these cells in the ascitic fluid of mice they are innoculated intraperitoneally at $10^7$ cells per mouse 2–4 weeks following intraperitoneal injection of 0.5 ml pristan.

Quantitation of Antibodies Against CT in Mouse Sera and in Hybridoma Growth Media The level of antibodies against CT in sera of mice is determined by measuring their neutralizing and binding activities.

CT Neutralizing Activity: (FIG. 2a)

Samples of CT (10 U in 50 μl Dulbecco's modified Eagle's medium containing 2% FCS (DMEM-2% FCS)) are incubated for 4 h at 37° with samples of mouse sera (50 μl), serially diluted in DMEM-2% FCS. They are then further incubated for 12–16 h at 4° C. and than assayed for CT activity at eight 2-fold dilutions.

CT Binding Activity: (FIG. 2b)

Samples of crude concentrated CT (30 μl, $10^4$ U/ml) are incubated for 4 h at 37° C. in conical-bottom micro-titer wells (Greiner) with samples of the mouse serum, serially diluted in DMEM-2% FCS. Normal mouse serum (20 μl of a 1:40 dilution in PBS) is added, followed by 60 ul of goat antiserum against mouse F(ab)'$_2$. The plates are further incubated for 30 min at 37° C. and then overnight at 4° C. and are then spun at 1200 g for 5 min at 4° C. The immunoprecipitates are rinsed twice with cold PBS and once with unbuffered saline, solubilized by adding 50 μl NH$_4$OH and assayed for CT activity at eight 2-fold dilutions.

The Solid Phase Assay for Detecting CT Binding Monoclonal Antibodies (applied in screening the hybridoma growth media for the presence of CT-binding antibodies, FIG. 3.). PVC microtiter plates (Dynatech, Alexandria, Va.) are incubated, with affinity purified goat antibody against mouse F(ab)$_2$ (80 μg/ml in PBS, 80 ul/well) then with samples of the hybridoma growth media (50 μl/well) and finally with samples of a crude concentrated CT preparation ($10^4$ U/ml, 50 μl/well). Each of the incubation periods is for 12–18 h (at 4° C.) and following each the plates are rinsed 3 times with PBS. The plates are then further rinsed once with unbuffered saline and the bound CT is dissociated by applying NH$_4$OH (75 mM containing 0.1% FCS 20 μl/well). A hundred ul of 0.04 M Na-Hepes pH 7.4 in DMEM-10% FCS are added and the eluted cytotoxic activity is quantitated on CHI-sensitized SV80 cells, at four, two-fold dilutions.

Purification of CT on Immunoadsorbents

Monoclonal antibodies are purified from ascitic fluids by precipitation with ammonium sulphate (50%). Those of the IgM isotype are further purified by dialysing against water followed by solubilitztion of the precipitating IgM in PBS. 10 mg of each of the immunoglobulins are coupled to 1 g Trisacryl GF2000 (LKB) which was derivitized with aminocaproic acid and activated with N-hydroxy succinimide. Uncoupled antibody is removed by washing the resin with 50 mM Na-citrate pH 2.8 and then with 0.15 NH$_4$OH.

For purification of CT on the immunoadsorbent, samples of 0.5 ml of the resin are mixed for 2 h at 4° C. with 3 ml of CT preparation in the presence of 0.5 M TMAC. The resins are then packed in small columns, unbound protein is washed with 0.5 M TMAC solution. The columns are then further washed with 0.5% NP-40 in 0.5M TMAC, then with a solution of 1 M Nacl, containing also 10 mM sodium phosphate buffer pH 7.4 and then with unbuffered saline and the bound CT is eluted by applying 0.2 M NH$_4$OH and neutralized with 1 M acetic acid within 10 min of elution. All steps of the immunoaffinity purification procedure are carried out at 4° C.

Analysis of the Purified CT by SDS Gel Electrophoresis

Figure 5:
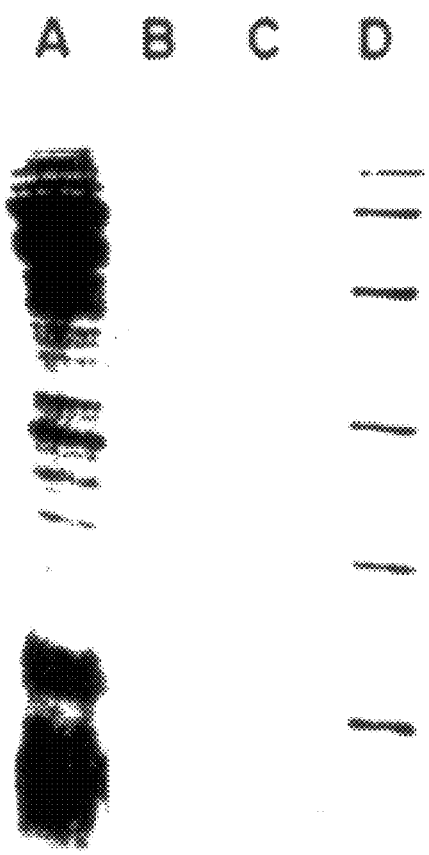
FIG. 5 shows in C the CT purified on an immunoadsorbent constructed from the monoclonal antibody, as detected by Coomassie blue staining, following electrophoresis on an acrylamide gel in the presence of SDS. (Also shown is the pattern of proteins in the crude preparation of lymphokines from which this CT has been purified, in A, the lack of any binding of protein when applying this crude preparation on an immunoadsorbent constructed from an irrelevant antibody, (against DNP) in B and molecular weight standards, in D).
Figure 6:
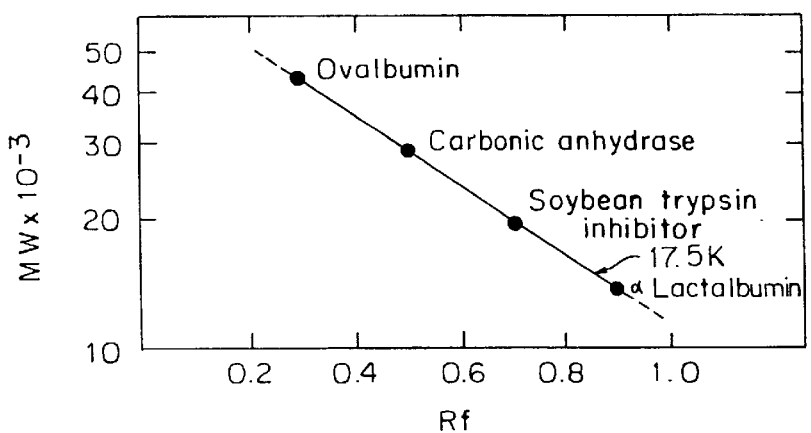
FIG. 6 shows how the molecular weight of this CT is estimated by comparision to the mobility, on that acrylamide gel, of the standard proteins shown in FIG. 5D. A selective cytotoxic effect of the CT and its enhancement by IFN are demonstrated in FIG. 7 which shows the cytotoxic effect of the CT at various concentrations on VSV-infected SV-80 cells (●) and its further enhancement by treating these cells with IFN-γ (10 U/ml, 16 hr prior to infection (○) or 100 U/ml. prior to infection (Δ)) in comparison to the resistance to CT observed in uninfected cells (■) even when they are also treated with IFN-γ at 100 U/ml (□).
Figure 7:
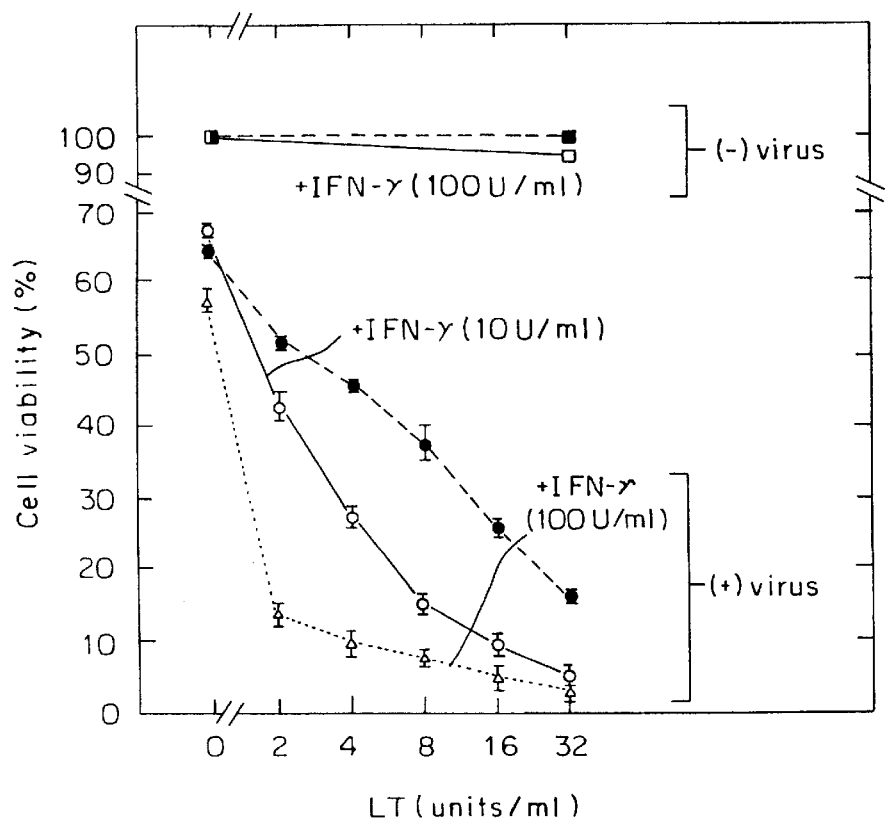

FIG. 5. shows the pattern of proteins in a crude preparation of cytotoxins as analyzed on SDS-polyacylamide gel (15%). Ammonia eluted fraction from an immunoadsorbent constructed from the antibody U13-6 (against DNP) on which the crude CT has been applied (in B). CT purified from the crude preparation of the CT-1 immunoadsorbent column (in C) and molecular weight standard (phosphorylase 94K, bovine serum albumin 67K, ovalbumin 43K, carbonic anhydrase 30K, soybean trypsin inhibitor 20.1K and lysozyme 14.4K daltons (in D) as shown in FIG. 6. FIG. 5c shows that the purififed CT constitutes a single polypeptide species of U. molecular weight of the purified protein as estimated by comparison to the mobility on the acrylamide gel of other proteins with known molecular weights, is about 17.5 Kd in FIG. 6.

What is claimed is:

1. A monoclonal antibody which specifically binds a human cytotoxin having a molecular weight of about 17,500 as determined by polyacrylamide gel electrophoresis, said cytotoxin being obtainable from stimulated human monocytes, said cytotoxin being further characterized by exhibiting a cytotoxic effect on cycloheximide-sensitized SV-80 cells and by being obtainable in a state of enhanced purity by adsorption of the cytotoxin from an impure preparation onto controlled pore glass beads, and subsequent desorption of the cytotoxin in a state of enhanced purity.

2. The antibody of claim 1 which is a murine monoclonal antibody.

3. The antibody of claim 1 which is produced by a hybridoma formed by a fusion of myeloma cells with spleen cells from a mammal previously immunized with a pure or impure preparation of said cytotoxin.

4. The antibody of claim 3 which is a murine monoclonal antibody.

5. A monoclonal antibody which specifically recognizes and binds a human cytotoxin having a molecular weight of 17,000±500 D as determined by polyacrylamide gel electrophoresis, said human cytotoxin being obtainable from stimulated human monocytes, said cytotoxin being further characterized by exhibiting a cytotoxic effect on cycloheximide-sensitized SV-80 cells.

6. The antibody of claim 5 which is a murine monoclonal antibody.

7. The antibody of claim 5 which is produced by a hybridoma formed by a fusion of myeloma cells with spleen cells from a mammal previously immunized with a pure or impure preparation of said cytotoxin.

8. The antibody of claim 7 which is a murine monoclonal antibody.

9. A monoclonal antibody which specifically recognizes and binds a human cytotoxin having a molecular weight of 17,000±500 D as determined by polyacrylamide gel electrophoresis, said human cytotoxin being obtainable from stimulated human monocytes, said cytotoxin being further characterized by being obtainable in a state of enhanced purity by adsorption of the cytotoxin from an impure preparation onto controlled pore glass beads, and subsequent desorption of the cytotoxin in a state of enhanced purity.

10. The antibody of claim 9 which is a murine monoclonal antibody.

11. The antibody of claim 9 which is produced by a hybridoma formed by a fusion of myeloma cells with spleen cells from a mammal previously immunized with a pure or impure preparation of said cytotoxin.

12. The antibody of claim 11 which is a murine monoclonal antibody.

* * * * *